United States Patent [19]

Eggertsen

[11] Patent Number: 4,826,771
[45] Date of Patent: May 2, 1989

[54] PROCEDURE TO BE PERFORMED IN CONJUNCTION WITH PROTEIN BLOTTING OR NUCLEIC ACID BLOTTING

[75] Inventor: Gösta Eggertsen, Uppsala, Sweden

[73] Assignee: Pharmacia AB, Uppsala, Sweden

[21] Appl. No.: 64,303

[22] PCT Filed: Oct. 8, 1986

[86] PCT No.: PCT/SE86/00461

§ 371 Date: May 27, 1987

§ 102(e) Date: May 27, 1987

[87] PCT Pub. No.: WO87/02386

PCT Pub. Date: Apr. 23, 1987

[30] Foreign Application Priority Data

Oct. 9, 1985 [SE] Sweden ................................. 8504666

[51] Int. Cl.⁴ ........................ G01N 35/00; C12Q 1/68; C12M 1/10

[52] U.S. Cl. ...................................... 436/45; 436/530; 436/507; 435/6; 435/310; 435/312

[58] Field of Search .................... 422/72; 436/45, 518, 436/530, 502, 509; 354/329–330; 435/6, 291, 310, 312

[56] References Cited

U.S. PATENT DOCUMENTS

| | | | |
|---|---|---|---|
| 3,626,834 | 9/1969 | Speranza | 354/329 |
| 3,950,134 | 4/1976 | Miles | 436/807 |
| 4,302,092 | 11/1981 | Ashton et al. | 354/329 |

*Primary Examiner*—Sidney Marantz
*Assistant Examiner*—Lyle Alfandary-Alexander
*Attorney, Agent, or Firm*—Fred Philpitt

[57] ABSTRACT

Procedure to be performed in conjunction with protein blotting or nucleic acid blotting wherein the matrix to which said components have been transferred is contacted with reagent and wash solutions in a rotary drum.

4 Claims, No Drawings

PROCEDURE TO BE PERFORMED IN CONJUNCTION WITH PROTEIN BLOTTING OR NUCLEIC ACID BLOTTING

BACKGROUND OF THE INVENTION

The present invention relates to a simplified procedure to be performed in conjunction with protein blotting or nucleic acid blotting, in that the medium to which said components have been transferred is contacted with reagent and washing solutions in a rotary drum.

When an electrophoretic separation is carried out the sample solution is usually applied onto a gel disk or plate having a thickness of about one millimeter or a few millimeters, whereupon the individual components of the sample are caused to migrate in the gel under the action of an electric field. For an identification and analysis of the separated components and, optionally, for treating them with suitable reagents it is imperative that the whole amount of the component contemplated is made available. Since in a so-called electrophoretic band the components are in a diffused state such as to extend into the interior of the gel—that is, they are distributed within the volume defined by the surface area of the band and the thickness of the gel—methods have been developed by which component molecules are transferred from the gel to the surface of a solid matrix, usually nitrocellulose paper. Such a transfer is generally referred to as "blotting". A blotted protein by being located on a surface rather than inside a gel is enabled to participate in a major number of interactions. Thus, for example, it may react with antibodies; this is an important feature for immunological purposes. Some prominent examples of such practical applications are Analysis of reactivities of various antibodies.

Analysis of antigenic structures of various types.

Identification of individual proteins present in mixtures, with the aid of specific antisera.

Antibodies bound to blotted proteins can be detected in various ways. A method frequently chosen involves the use of a labeled secondary antibody directed against the primary antibodies. Such a secondary antibody may be for instance antirabbit-IgG in cases where the primary antibody source is rabbit serum. Labeling of the antibody may be effected with the aid of some radioactive isotope, fluorescent compounds or certain types of enzymes. In this latter case the enzyme position on the solid matrix is stained by after-treatment with suitable substrates. An increased degree of sensitivity may sometimes be obtained by the use of a secondary antibody which is allowed to react with a labeled reagent in a third step. Recent techniques employ for example biotin-labeled secondary antibodies which will react in a third step with the protein avidin; this has multiple binding sites for biotin and has attached to it an enzyme as for instance, in most cases, either alkaline phosphatase or peroxidase. With this technique it is possible to detect amounts of protein down to about 100–200 picograms.

From the above explanations it will be appreciated that the protein that has been transferred to a solid matrix by way of blotting will be subjected to a major number of treating steps in connection with reactions of the kinds indicated above. Such treatments thus may involve three or more reagent solutions plus intercalated washing steps. This procedure is carried out, according to current techniques, in that the matrix containing the blotted proteins is incubated in boxes or sealable plastic bags on various types of shaker or rocker devices, the reagents/wash liquors being exchanged after predetermined periods of times. Frequently a plurality of samples are analyzed in parallel tests in which one or more of the treating steps may be the same. In cases where the protein is to be treated with three reagent solutions and three rinses in succession this will be found to involve a sequence of twelve treating steps; it will be readily appreciated that this is a cumbersome and lengthy procedure, with present techniques. Note moreover that a certain minimum amount of reagent is required for carrying out an effective incubation; and in order to suit the types of containers currently employed this minimum amount unfortunately has to be a relatively large volume. This is a significant disadvantage since some reagents are very expensive and may be available in only minute amounts - as e.g. certain types of antibodies.

Summary of the Invention

Thus, in contexts of blotting techniques there is a need for a procedure by which the number of operational handling steps is reduced;

reproducibility is improved due to more efficient rinsing and incubation;

reagent consumption is reduced.

We have now found that the aforesaid desiderata are fulfilled if an incubation/rinsing system is employed in which the solid medium is placed against the interior wall of a rotary drum and is contacted with the desired solution while the drum is rotating.

DESCRIPTION OF THE PREFERRED EMBODIMENT

The drum, preferably made of a transparent material like, for instance, plexiglass, is given a dimension such as to be suitable for the dimension of the strips to be treated. The diameter may be for example 5–10 cm, the circumference then being about 20–75 cm, and the length may be for example 5–11 cm, depending on how many strips are to be juxtaposed. The cylindrical interior surface is smooth but is provided with a ledge running parallel to the cylinder axix, the short edges of the strips being arranged to rest against the ledge during rotation. Moreover, the cylindrical interior surface may be provided with removable pins secured in threaded holes along concentric circles on the cylinder wall to thus prevent the strips from moving in their lateral direction during the rotational movement. The drum on at least one of its ends has a lid which is sealed by means of, for instance, an O-ring and through which the strips are inserted. Long drums will preferably have such a lid at each of their ends. Prior to the incubation and rinsing steps the drum, with its center line lying in a horizontal plane, is placed into some kind of known device for rotating cylindrical bodies, e.g. onto two rollers one of which is arranged to entrain the other bodies into rotational movement by means of friction.

After the blotting step the receiver matrix, e.g. nitrocellulose paper, is divided into strips of a desired width and length which are then placed (optionally after some operational step not common to all of the strips) against the cylindrical interior surface with their short ends lying against the aforesaid ledge and with their long sides extending in the direction of rotation. If desired the strips are immobilized laterally by means of the pins described above.

Reagent and rinse solutions are applied at the bottom of the drum so that during rotation the strips will be contacted by each respective solution during a period of each revolution. In a preferred embodiment of the invention the drum is filled only partially with the solution contemplated, this being a much more efficient procedure as compared to the case where the strips move in the solution during the entire rotation. It is advantageous to employ an amount of liquid considerably less than 50 % of the drum volume, preferably only about 5-10%. The speed and duration of rotation are adapted accordingly, so as to produce the desired reaction conditions.

As mentioned above, the procedure of this invention is well suited also to the performance of nucleic acid analyses, e.g. analyses of membrane-immobilized nucleic acids by DNA-DNA hybridizing or alternatively DNA-RNA hybridizing, the probe in each case being labeled so as to be detectable. The nucleic acid may be either applied directly on the membrane (so-called dot blot) or may be transferred from an electrophoretic gel be means of some eligible transferring technique. Contacting of the nucleic acid as required with prehybridizing solution, hybridizing solution and wash solutions is carried out in a manner analogous to the procedure described above.

In order to increase efficiency further the procedure of the invention may be supplemented with temperature control such as to make the reactions proceed at a given constant temperature.

The invention is accordingly related to a procedure to be performed in conjunction with blotting of proteins and nucleic acids. Strips containing the actual compounds are placed in the rotational direction onto the cylindrical interior wall of a drum arranged with its cylinder axis in the horizontal plane, whereupon the drum is rotated and the strips are contacted, during a period of each revolution, with a supply of wash solution or reagent solution present in the drum.

This method for processing blotted substances, selected from the group consisting of proteins and nucleic acids, by means of treating said blotted substances with treating liquids selected from the group consisting of wash liquids and reagent liquids is preferrably carried out in the following steps:

(i) placing at least one strip containing the blotted substances against the interior wall surface of a cylindrical rotary drum lying with its axis in a horizonal position, the strips beeing arranged on the drum wall surface so as to extend longitudinally in the rotational direction of the drum (ii) introducing a treating liquid into the drum and after steps (i) and (ii)

(iii) rotating said drum containing the strips and the treating liquid

In a preferred embodiment step (i) is carried out before step (ii).

The invention is illustrated by the following non-limitative example.

EXAMPLE

Screening of monoclonal mouse antibodies directed against human C3

Complement factor C3 is one of the most essential components of the so-called complement system; it is a protein consisting of two chains and having a total molecular weight of about 185,000.

About 200 µg of reduced C3 and try-C3c (a fragment of C3 obtained by trypsin digestion) were applied to a polyacrylamide gel (11% gel with 4.8% spacer) for SDS electrophoresis according to Neville et al., Methods in Enzymology 32 (1974), p. 92-102. Separated polypeptides were electroblotted onto nitrocellulose paper (NAHY) 304F0; Millipore Corp., Bedford, USA. Quenching and dilution of overlays were carried out in 10% heat-inactivated calf serum (0.02 M phosphate buffer, 0.15 M NaCl and 0.2% Tween 20). The rinsing steps were carried out in 0.5% bovine serum albumin (0.02 M phosphate buffer, 0.15 M NaCl and 0.1% Tween 20). The nitrocellulose paper was cut into strips of 5 mm width. Of these, Nos. 1-7 were incubated with various different monoclonal antibodies in 1/100 dilution (3 ml/strip in sealable plastic bags on rockers in a cold room, for one night). Strip No. 8 which served as a reference was incubated with 3 ml of antibodies against try-C3c (1/1000). The strips were then transferred to a drum according to the present invention and rinsed three times with 10 ml of solution - each time for 5 minutes - whereupon they were incubated with 5 ml of biotin-labeled rabbit-antimouse-IgG (1/500 dilution) for 1 hour at room temperature. This was then followed by rinsing as above and then again incubation which was carried out this time with 5 ml solution of avidin coupled to peroxidase (Sigma Chem, St. Louis, Mo., USA. Thereafter the washing procedure was repeated prior to staining with 4-chloro-1-naphthol (Anal. Biochem. 119 (1982) p. 142-147).

The results of this procedure were clearly comparable with corresponding results after traditional blotting despite the very great procedural simplification achieved by way of the present invention.

I claim:

1. In a method for processing at least one paper strip containing at least one blotted substance selected from the group consisting of proteins and nucleic acids, which method includes treating said paper strip and blotted substance with a treating liquid selected from the group consisting of a wash liquid and a reagent liquid, the improvement which consists essentially of the steps of (i) placing at least one paper strip containing at least one of said blotted substances against the interior wall surface of a cylindrical rotary drum that is disposed with its axis in a horizontal position, said at least one paper strip being arranged on the drum wall surface so as to extend in the rotational direction of the drum, (ii) introducing a treating liquid into the interior of the drum after step (i), and (iii) rotating said drum about its axis after steps (i) and (ii) so as to bring said treating liquid into contact with said at least one paper strip, the lateral flow of said treating liquid being unrestricted within said rotary drum.

2. A method according to claim 1 wherein less than 50% of the internal drum volume is filled with said treating liquid.

3. A method according to claim 1 wherein 5-10% of the internal drum volume is filled with said treating liquid.

4. A method according to claim 1 wherein said strip is paper.

* * * * *